United States Patent [19]

Brinkmann

[11] Patent Number: 4,852,385

[45] Date of Patent: Aug. 1, 1989

[54] MAINTENANCE DEVICE FOR AT LEAST PARTIALLY AUTOMATIC CLEANING AND CALIBRATION OF A PROBE CONTAINING A MEASURED VALUE TRANSMITTER

[75] Inventor: Heinz J. Brinkmann, Frankfurt am Main, Fed. Rep. of Germany

[73] Assignee: Dr. W. Ingold AG, Urdorf, Switzerland

[21] Appl. No.: 15,859

[22] PCT Filed: May 28, 1986

[86] PCT No.: PCT/CH86/00070

§ 371 Date: Jan. 27, 1987

§ 102(e) Date: Jan. 27, 1987

[87] PCT Pub. No.: WO86/07151

PCT Pub. Date: Dec. 4, 1986

[30] Foreign Application Priority Data

May 30, 1985 [CH] Switzerland .................. 2279/85

[51] Int. Cl.[4] ............... G01N 27/30; G01N 27/38; G01D 18/00
[52] U.S. Cl. .................... 73/1 R; 204/401; 204/408
[58] Field of Search ........... 73/1 R, 1 G; 204/401, 204/408, 433, 403, 1 H, 1 T

[56] References Cited

U.S. PATENT DOCUMENTS

| | | | |
|---|---|---|---|
| 3,625,850 | 12/1971 | Arrington | 204/195 |
| 4,260,950 | 4/1981 | Hadden et al. | 73/1 R X |
| 4,299,495 | 11/1981 | Sawakata et al. | 356/442 |
| 4,336,232 | 6/1982 | Moritz | 423/164 |

FOREIGN PATENT DOCUMENTS

| | | |
|---|---|---|
| 2514193 | 1/1976 | Fed. Rep. of Germany . |
| 2557542 | 6/1977 | Fed. Rep. of Germany . |
| 2712159 | 9/1978 | Fed. Rep. of Germany . |
| 3118771 | 11/1982 | Fed. Rep. of Germany . |

OTHER PUBLICATIONS

*Patent Abstracts of Japan;* vol. 6, No. 229, (1107) p. 155; published Nov. 16, 1982; (English Abstract of Japanese Patent Publication 57-132053 dated Aug. 16, 1982).

*Primary Examiner*—Tom Noland
*Attorney, Agent, or Firm*—Werner W. Kleeman

[57] ABSTRACT

The combination of a measured value transmitter unit, a metering unit and a control unit enables all maintenance measures which become necessary during the course of process monitoring, to be carried out with little expenditure of labor and time and without removing the sensor from the container containing the measured medium. In addition, this combination, in which all functions necessary for carrying out the maintenance can be initiated and/or controlled by pneumatic signals, permits at least partial automation of the maintenance.

11 Claims, 4 Drawing Sheets

MAINTENANCE DEVICE FOR AT LEAST PARTIALLY AUTOMATIC CLEANING AND CALIBRATION OF A PROBE CONTAINING A MEASURED VALUE TRANSMITTER

BACKGROUND OF THE INVENTION

The present invention relates to a new and improved construction of a maintenance device for at least partially automatic cleaning and calibration of a probe containing a measured value transmitter.

In its more specific aspects, the present invention particularly relates to a new and improved construction of a maintenance device for at least partially automatic cleaning and calibration of a probe containing a measured value transmitter and which probe containing the measured value transmitter is part of a measuring device for continuously monitoring biological or chemical processes. Such processes are continuously monitored by measuring analytical parameters in a fluid medium. The probe contains a sensor which is removable from the fluid medium to be investigated, and a guide device for holding and guiding the sensor of the probe which contains the measured value transmitter, between an operative position and a maintenance position. The probe further contains a shut-off device for shutting off the probe from the fluid medium to be investigated.

In general, the aforementioned probes contain, for example, electrochemical sensors, such as pH electrodes, particularly single-rod electrode assemblies, and are used for monitoring biological or chemical processes, particularly fermentation processes. It is disadvantageous here that, in practice, the aforementioned sensors only have a limited service life and their indication is subject to change in the course of time, namely for the following reasons:

1. contamination by the reaction medium;
2. zero-point drift;
3. loss of gradient in the case of pH electrodes, shift of the reference voltage in the case of pH and redox electrodes, and deactivation in the case of redox electrodes; and
4. total failure of the electrode.

The interferences caused thereby hitherto have rendered more difficult and partially impossible the continuous monitoring of biological and chemical processes because they lead to a considerable falsification of the measured values and the frequently necessary removal and replacement of the sensor brings about an interruption of the process course.

In order to eliminate the interferences arising due to the contamination mentioned as reason 1. hereinbefore, continuous or discontinuous cleaning methods have been proposed or used in the past. These include:

1.1 discontinuous chemical cleaning using agents which clean the sensor membrane;
1.2 continuous cleaning using water which is sprayed from rinsing nozzles against the sensor or electrode membrane;
1.3 mechanical continuous or discontinuous cleaning using rotating brushes or ultrasound.

The aforementioned cleaning methods have several disadvantages. Thus, for example, the pH value is highly falsified using the cleaning method mentioned hereinbefore as method 1.1, and the cleaning agent generally is diluted by the fluid medium. The consumption of cleaning agent also is relatively high. The cleaning method mentioned hereinbefore as method 1.2, generally only works for loosely adhering contaminants which is why this method can only be used to a limited extent. In addition, the pH value is also falsified in this case. The cleaning method mentioned hereinbefore as method 1.3, is associated with great mechanical complexity and, in the case of abrasive media, with high wear of the moving parts. Ultrasound cleaning requires a relatively large constructional volume and, in addition, cannot be used in areas with an explosion hazard due to the high energy output. Besides the disadvantage that the aforementioned cleaning methods require relatively large constructional volumes and are not suitable for small or restricted installation dimensions, there is added the further disadvantage that their effectiveness is not always guaranteed at high pressures.

The elimination of errors which are caused in the course of time by the reasons mentioned hereinbefore as reasons 2. and 3., requires regularly repeated cleaning and calibration operations using at least two calibration solutions and corrections at the measuring instruments. The operations necessary for the elimination of these errors require a time expenditure of a few hours to several weeks, depending on the type of fluid medium to be investigated, the type of the contaminants, and the magnitude of the occurring electrode drift. However, this means that these operations result in considerable impairment of the process to be monitored and thus causes a considerable increase in costs.

It is known from German Patent Publication No. 2,557,542, published June 23, 1977, that a measuring electrode may be installed into a ball valve which separates the measuring electrode from the medium to be investigated. The ball valve position is changed in order to make the measuring electrode accessible for cleaning or calibration solutions. Furthermore, there is known from German Patent Publication No. 2,712,159, published Sept. 28, 1978, that the fluid medium to be investigated and calibration solutions can be sprayed onto the measuring electrode in small quantities through fine nozzles. Furthermore, from German Patent Publication No. 2,514,193, published Jan. 2, 1976, there is known an instrument for automatic analysis of liquid samples in which instrument test tubes containing the samples are arranged on a conveyor belt which is subdivided into sectors. By means of such conveyor belt, the test tubes are conveyed to individual analysis stations in accordance with a predetermined program. The control here preferably is effected by means of a pneumatic programming mechanism. Finally, it has been proposed that the electrode membrane be accommodated in a recess in which the electrode can be cleaned or calibrated when necessary.

These aforementioned methods are afflicted with various deficiencies, especially as they are obviously not universally applicable. Thus, for example, the arrangement according to German Patent No. 2,557,542 is only suitable for tubes. In the case of automation, a bypass would have to be installed. In addition, no information is given regarding the means and the manner in which the infeed of cleaning and calibration solutions and their metering is accomplished. In addition, during use of these methods, the temperature of the calibration solutions used is not taken into account, which leads to an impairment in the calibration accuracy which cannot be neglected.

SUMMARY OF THE INVENTION

Therefore, with the foregoing in mind, it is a primary object of the present invention to provide a new and improved construction of a maintenance device for at least partially automatic cleaning and calibration of a probe containing a measured value transmitter and which maintenance device is not affected with the drawbacks and limitations of the prior art constructions heretofore discussed.

Another important object of the invention is to provide a new and improved construction of a maintenance device for at least partially automatic cleaning and calibration of a probe containing a measured valve transmitter and which maintenance device permits simple and insignificantly labor-intensive and time consuming cleaning and calibration operations on the sensor of the probe as well as partial or complete automation of the maintenance operations.

Now in order to implement these and still further objects of the invention, which will become more readily apparent as the description proceeds, the maintenance device of the present development is manifested by the features that, a measured value transmitter unit includes the probe which contains the measured value transmitter and an external tube, and can be closed by means of a shut-off device. The sensor is displaceably arranged within the external tube and can be pneumatically displaced. A metering unit is provided for infeeding at least one rinsing or cleaning liquid and at least one buffer solution which constitutes a calibrating liquid. A control unit contains control elements for transmitting pneumatic signals in order to trigger and/or control all functions of the measured value transmitter unit and the metering unit as well as indicators for monitoring such functions and indicating faults. The measured value transmitter unit and the metering units are coupled to the control unit by means of compressed air conduits for transmitting the pneumatic signals.

Due to the combination of the measured value transmitter unit, metering unit and control unit it is achieved that the entire maintenance program is attained at little consumption of labor and time and without removing i.e. disassembling the sensor from the container containing the fluid medium to be investigated. In addition, in this combination all functions necessary for carrying out the maintenance operation are triggered and/or controlled by means of pneumatic signals and the coupling to a control unit is effected by means of compressed air conduits. There are thus rendered possible at least partial automation of the maintenance and continuous monitoring of the entire maintenance program in a simple fashion.

Contamination or dilution of the fluid medium by the rinsing or cleaning fluid used and/or the buffer solutions used as calibration fluid or an alteration in the pH value of the buffer solutions by the fluid medium can be prevented when the probe which contains the measured value transmitter, comprises an actuating member for displacing the sensor of the probe. Such actuating member is coupled to the shut-off device and guided by means of a guide device. The actuating member is controlled by means of the pneumatic signals which issue from the control unit.

The metering unit comprises an infeed system for infeeding rinsing or cleaning fluid and thus permits accurate metering of the infeed of the rinsing or cleaning fluid and the buffer solutions as well as setting a time limit for the infeed of the rinsing or cleaning fluid and the buffer solutions. Such feed system is equipped with a pressure controller which is coupled to the control unit via compressed air conduits, and a directional control valve which is coupled to the control unit via a compressed air conduit. Furthermore, first and second storage vessels which are equipped with respective sensors and respectively contain first and second buffer solutions, are connected to respective first and second metering pumps. The sensors of the first and second storage vessels as well as the first and second metering pumps are coupled to the control unit by means of respective compressed air conduits. This construction thus permits continuous monitoring of the rinsing or cleaning fluid pressure and the presence of sufficient amounts of the buffer solutions.

All the steps which are necessary for carrying out the maintenance operation, can be carried out in a simple manner and with little time consumption when the control unit contains control elements for controlling the following functions: (i) Displacement of the sensor between the operative or measuring position and the maintenance position, (ii) initiation or repetition of the cleaning and calibrating operations, and (iii) infeed of the rinsing or cleaning fluids and the buffer solutions.

In the inventive construction, the control unit preferably comprises pneumatic indicators for indicating the momentary position of the sensor and the momentary operating step of the maintenance program, as well as alarm indicators for indicating faults during the infeed of the rinsing or cleaning fluid and/or the buffer solutions. There are thus continuously monitored all the operating steps and measured values which are necessary for successfully carrying out the maintenance operation.

Inaccuracies caused by unnoticed temperature differences in the buffer solutions or in the reaction medium, can be avoided when the control unit has two separate inputs for two temperature compensation resistances. One of the temperature compensation resistances is arranged in the probe which contains the measured value transmitter, and provided for compensating temperature variations in the buffer solutions. The other temperature compensation resistance is arranged in the fluid medium to be investigated and provided for compensating temperature variations in such fluid medium.

In an advantageous construction, the control unit is coupled to a central compressed air supply and thus enables simultaneous and uniform initiation and monitoring of all functions of the measured value transmitter unit and the metering unit. It is of particular advantage in this construction that the connection of the control unit with the central compressed air supply can be effected via a simple plug-type connection.

Fully automatic execution of the entire maintenance program and complete adaptation thereof to the course and the requirements of the process to be monitored are enabled when the compressed air conduits are equipped with solenoid valves to be electrically operated, pneumatic-electric transducers are provided for converting pneumatic signals into electrical signals, and the control unit is connected to a central process control.

In the inventive maintenance device electrochemical or optical sensors are selectively employed depending upon the type of the measurement process to be carried out in each individual case. This selection allows the use of the maintenance device within a wide field of applications.

BRIEF DESCRIPTION OF THE DRAWINGS

The invention will be better understood and objects other than those set forth above will become apparent when consideration is given to the following detailed description thereof. Such description makes reference to the annexed drawings wherein throughout the various Figures of the drawings there have been generally used the same reference characters to denote the same or analogous components and wherein.

DETAILED DESCRIPTION OF THE PREFERRED EMBODIMENTS

Describing now the drawings, it is to be understood that only enough of the construction of the maintenance device has been shown as needed for those skilled in the art to readily understand the underlying principles and concepts of the present development, while simplifying the showing of the drawings. Turning attention now specifically to FIG. 1 of the drawings, there has been illustrated therein by way of example and not limitation in a schematic block diagram, a maintenance device for trouble-free, at least partially automatic cleaning and calibration of a probe which contains a measured value transmitter and a sensor coupled therewith. The probe forms part of a measuring device suitable for continuously monitoring biological or chemical processes by measuring analytical parameters in a fluid medium. The maintenance device particularly includes a measured value transmitter unit A1, a metering unit A2 and a control unit A3. The measured value transmitter unit A1 is equipped with a coupling member B1 for connection to the metering unit A2 and with a multipole coupler C1 for coupling to the control unit A3. The metering unit A2, in turn, contains a coupling member B2 which is compatible with the coupling member B1, and a multipole coupler C2 for coupling to the control unit A3. The control unit A3 is provided with multipole couplers C 3.1 and C 3.2. The multipole coupler C 3.1 of the control unit A3 is compatible with the multipole coupler $C_1$ of the measured value transmitter unit A1. The multipole coupler C 3.2 of the control unit A3 is compatible with the multipole coupler $C_2$ of the metering unit A2. In addition, the control unit A3 contains a signal output D through which the control unit A3 can be connected to a central compressed air supply or, additionally and via pneumatic/electric transducers, to a central process control unit.

Figure 2:
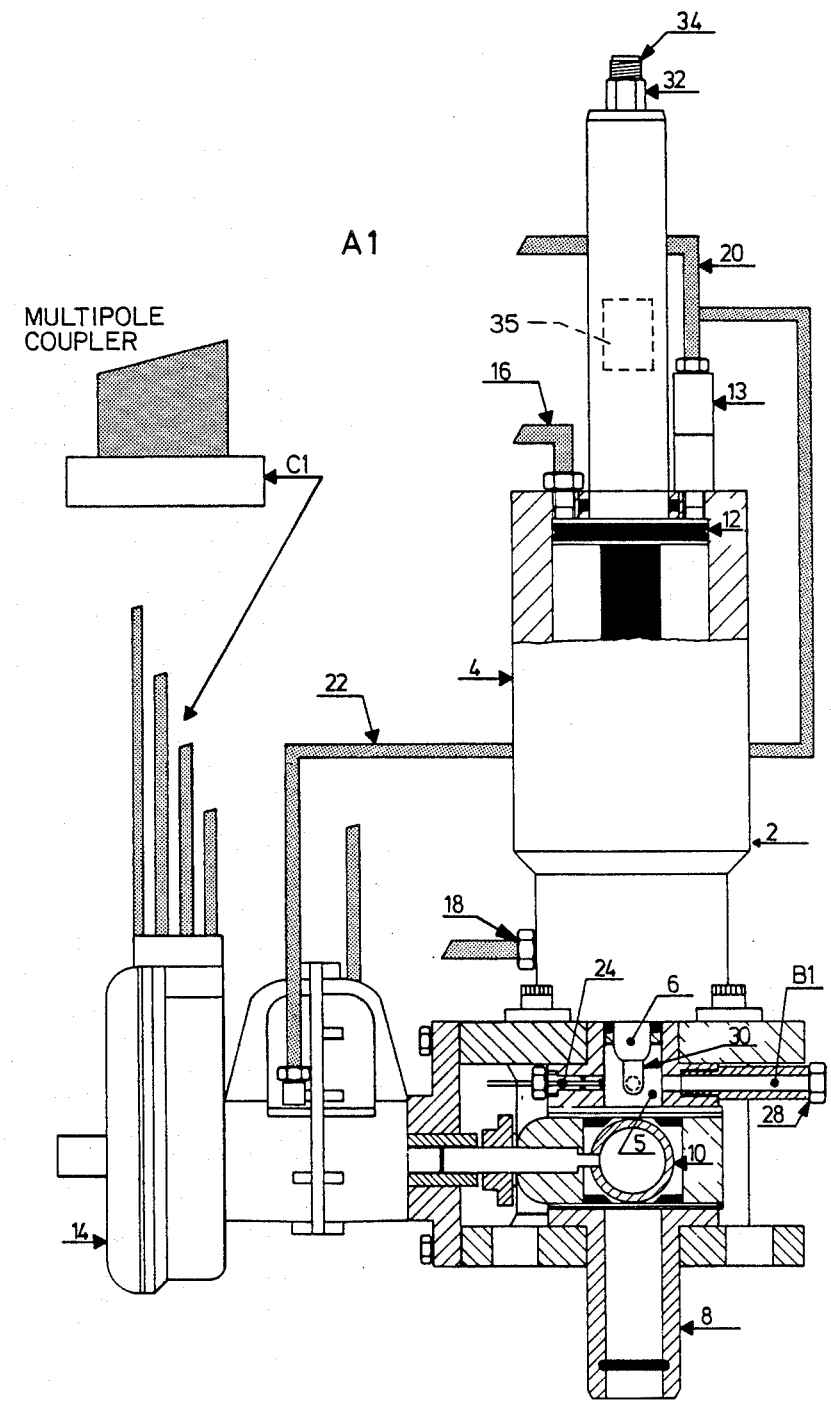
FIG. 2 shows, partially in vertical longitudinal section, a measured value transmitter unit of the maintenance device shown in FIG. 1.

FIG. 2 shows a probe 2 containing the measured value transmitter as schematically indicated by reference character 35 and the sensor and forming the essential component of the measured value transmitter unit A1. The probe 2 contains an external tube 4 in which the sensor 6, for example a pH electrode, is displaceably arranged. In the illustrated position, the sensor 6 is displaced such as to be located in a rinsing chamber 5 At its head part the probe 2 is connected to a guide bush 8 of a container containing the fluid medium to be investigated and the external tube 4 carries a shut-off device 10, for example, a ball valve for preventing the fluid medium from flowing out into the open. Furthermore, a guide device 12 is coupled to the shut-off device 10 and accommodated in the external tube 4. The guide device 12 serves to hold and guide the sensor 6 during displacement between an operative position in which the sensor 6 is immersed into the fluid medium through the opened shut-off device 10, and a maintenance position in which the sensor 6 is retracted into the external tube 4 and the shut-off device 10 is closed. The guide device 12 is coupled to actuating members 13 and 14 for displacing the sensor 6 in the direction of the longitudinal axis of the probe 2. The sensor 6 thus can be displaced between the aforementioned operative position and maintenance position by means of compressed air infed via compressed air conduits 16 or 18, as the case may be. Outlet conduits 20 and 22 are provided for venting the compressed air from the external tube 4.

Figure 1:
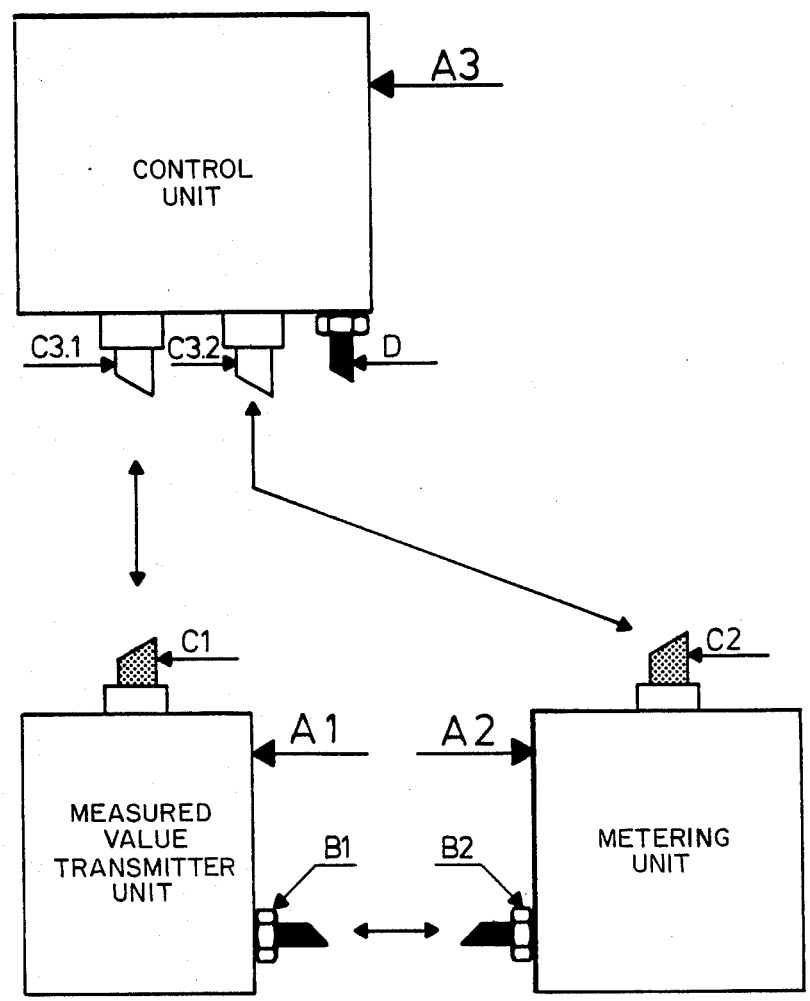
FIG. 1 shows a block diagram of an exemplary embodiment of the inventive maintenance device.

A temperature compensation resistance 24 is arranged in the rinsing chamber 5 and the resistance values of this temperature compensation resistance are supplied to the control unit A3. The rinsing chamber 5 contains an inlet aperture provided with a check valve 28 in the region in which the head part of the probe 2 and a membrane 30 of the sensor 6 are located. The sensor 6 is surrounded by an inner tube 32 which is fixedly connected, at an end part of the probe 2 opposite to its head part, to a plug connector 34 for connection to a measuring instrument. The inlet aperture corresponds to the coupling member Bl which is shown in FIG. 1 and connects the measured value transmitter unit A1 to the metering unit A2 via the coupling member B2 of the metering unit A2 in order to infeed rinsing or cleaning agent and/or buffer solutions from the metering unit A2 into the rinsing chamber 5 of the measured value transmitter unit A1. A multipole coupler which corresponds to the multipole coupler Cl shown in FIG. 1, is compatible with the multipole coupler C 3.1 of the control unit A3, and is provided for coupling thereto the actuating members 13 and 14 through the compressed air conduits 16, 18, 20 and 22.

Figure 3:
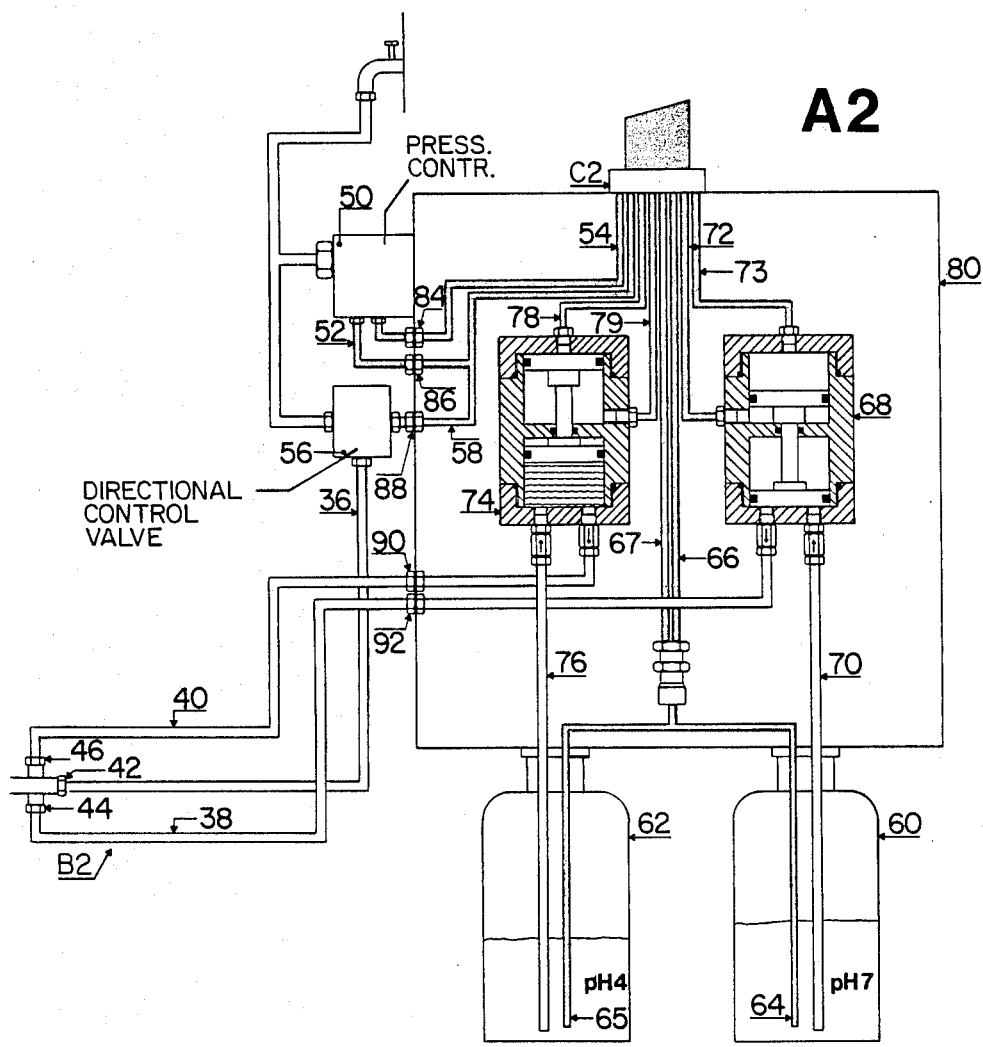
FIG. 3 shows, partially in vertical longitudinal section, a metering unit of the maintenance device shown in FIG. 1.

FIG. 3 shows the metering unit A2 which, in the exemplary embodiment is designed for using water as the rinsing or cleaning agent and two buffer solutions having different pH values. An infeed conduit system 48 in such metering unit A2 is formed by conduits 36, 38 and 40 which are equipped with check valves 42, 44 and 46, and corresponds to the coupling member B2 shown in FIG. 1. For monitoring and controlling the water pressure, there are installed in the water infeed conduit 36 a pressure controller 50 which is coupled to the control unit A3 via compressed air conduits 52 and 54, as well as a pneumatically operated directional control valve 56 which is coupled to a time control valve in the control unit A3 for adjusting the duration of the water infeed. The water can be withdrawn from a storage container or a water supply conduit.

In addition, the metering unit A2 contains a first storage vessel 60 containing a first buffer solution having, for example, a pH value of 7 and a second storage vessel 62 containing a second buffer solution having, for example, a pH value of 4. A sensor 64 is arranged in the first storage vessel 60, and a sensor 65 is arranged in the second storage vessel 62, the sensors 64 and 65 being coupled to the control unit A3 via compressed air conduits 66 and 67. For feeding the first buffer solution, there is provided a first metering pump 68, in the present case a piston pump. The first metering pump 68 is connected to the first storage vessel 60 via a conduit 70 and coupled to the control unit A3 via compressed air conduits 72 and 73. For feeding the second buffer solution, there is provided a second metering pump 74, in the present case a piston pump, which is identical to the first metering pump 68. The second metering pump 74 is connected to the second storage vessel 62 via a conduit 76 and is coupled to the control unit A3 via compressed air conduits 78 and 79.

A part of the metering unit A2 and which part encompasses the first and second storage vessels 60 and 62 and the respective first and second metering pumps 68 and 74 with the associated compressed air conduits 66, 67, 72, 73, 78 and 79, is installed in a housing 80 which contains the multipole coupler C2, passages 84, 86 and 88 for the compressed air conduits 52, 54 and 58, and tube connections 90 and 92 for the infeed conduits 38 and 40.

Figure 4:
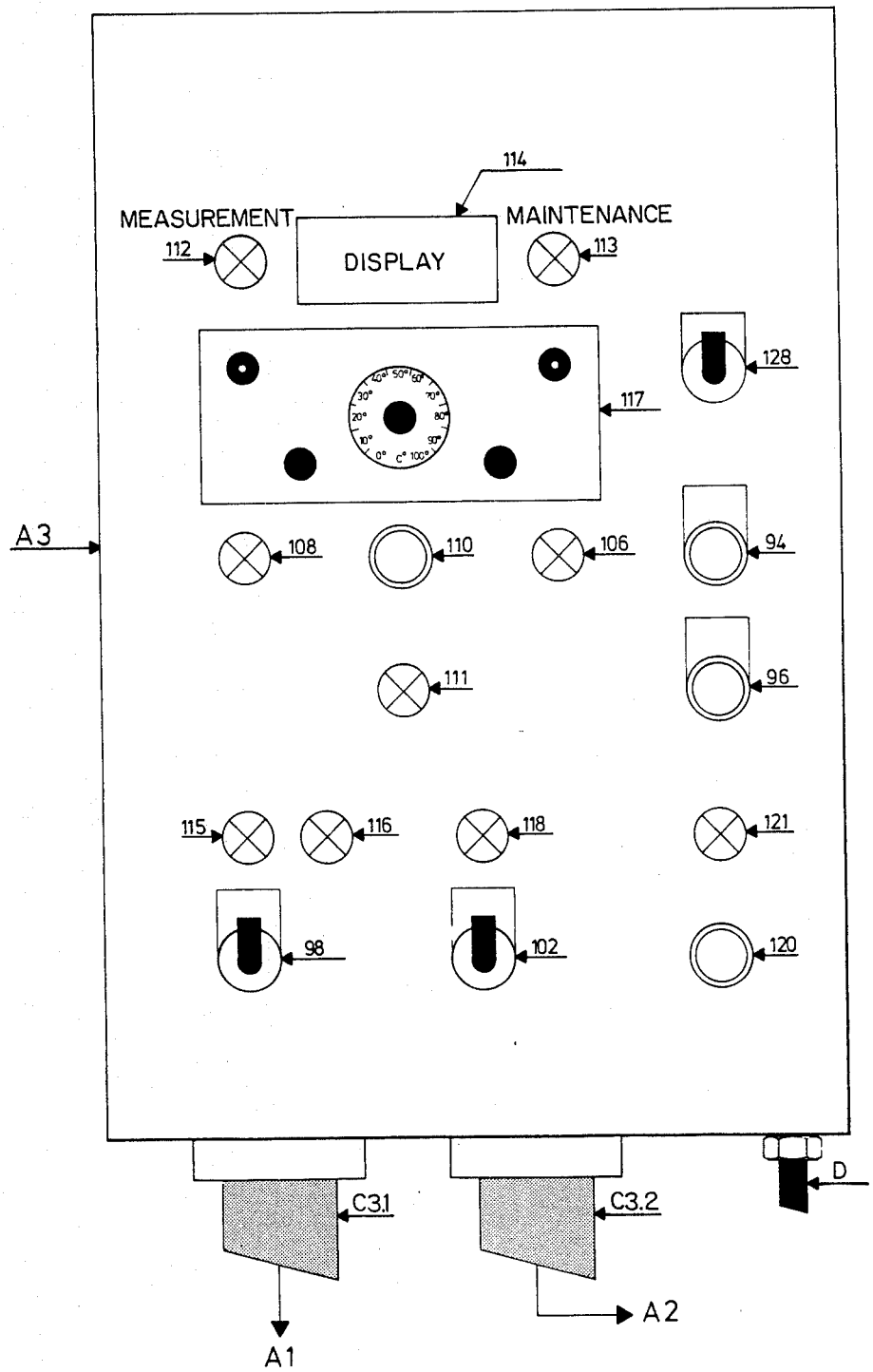
FIG. 4 shows, in top plan view, a control unit of the maintenance device shown in FIG. 1.

The control unit A3 is illustrated in FIG. 4 and contains control elements 94 and 96 for inserting and withdrawing the sensor 6, a control element 98 for switching on and off the rinse or cleaning system, a control element 102 for switching on and off the calibration program, a first request indicator 106 requesting the pH value to be set to 7.00, a second request indicator 108 requesting the pH value to be set to, for example 4.01, an ACKNOWLEDGE control element 110, pneumatic indicators 111, 112, 113 and 115 from which the current status of the program course can be read, an LCD display 114 from which the instant value measured by the sensor 6 can be read, an alarm indicator 116 indicating insufficient rinsing or cleaning water pressure, an amplifier 117 for setting the pH value, an alarm indicator 118 indicating an insufficient filling state of the storage vessel or container 60 and/or 62, a CALIBRATION control element 120, a pneumatic CALIBRATION indicator 121, a multipole coupler corresponding to C3.1 in FIG. 1 and compatible with the multipole coupler $C_1$ of the measured value transmitter unit A1, a multipole coupler corresponding to C 3.2 in FIG. 1 and compatible with the multipole coupler C2 of the metering unit A2, and a signal output corresponding to D in FIG. 1 and which signal output D can be coupled to a central compressed air supply or an additional central process control unit. In addition, the control unit A3 is equipped with two separate inputs which are not illustrated in the Figure, for connection with the temperature compensation resistance 24 and a further not-illustrated temperature compensation resistance which is located in the fluid medium to be investigated, as well as a control element 128 for switching from automatic temperature compensation to manual temperature compensation.

In the construction of the heretofore described control unit 43, all or most of the control elements are designed as push buttons. The color of indication is blue, with the exception of the MEASUREMENT indication which appears in green. The alarm indicators indicating insufficient rinsing or cleaning water pressure and/or an inadequate filling state of the first and second storage vessels or containers 60, 62 for the buffer solutions appear red. Further details in this respect follow further hereinbelow in the description of the operation of the exemplary embodiment.

The construction of the inventive maintenance device described hereinbefore with reference to FIGS. 2 to 4, is designed for semiautomatic operation. All of the operating steps as well as all response members are initiated or triggered by pneumatic signals. In a construction designed for fully automatic operation, the manually or pneumatically operated valves are replaced by electrically controlled solenoid valves. Similarly all pneumatic response members are replaced by PE, i.e. pneumatic-electric transducers which convert a pneumatic signal into an electric signal. By means of such pneumatic-electric interfacing the maintenance device and the probe 2 with the measured value transmitter and the sensor 6 as a whole can be connected to and controlled by a central process control unit, for example, a computer or a microprocessor-driven pH amplifier.

The operation of the exemplary embodiment will now be described with reference to the steps of rinsing or cleaning and calibrating a pH electrode which constitutes the sensor 6 shown in FIG. 2 and is utilized for monitoring a fermentation process. The maintenance device is designed for semiautomatic operation. The pH electrode 6 initially is located in the operative position i.e. immersed through the opened shut-off device 10 into the fluid medium to be investigated and this is indicated by the activated MEASUREMENT indicator 112 (green). For starting the rinsing or cleaning and calibrating operation, the pH electrode 6 is withdrawn from the fluid medium to be investigated into the rinsing chamber 5 by operating the push button 96; this is indicated by the activated MAINTENANCE indicator 113 (blue). The shut-off device 10, in the present case a ball valve, closes; the rinsing chamber 5 of the probe 2 containing the sensor 6, i.e. the pH-electrodes of the measured value transmitter is thereby closed to the fluid medium. The pH electrode 6 now is located in the maintenance position.

The rinsing or cleaning operation is started by actuating the control element 98 which constitutes a toggle switch in the illustrated embodiment. The calibrating operation is started by actuating the control element 102 which constitutes a toggle switch in the illustrated embodiment. The directional water control valve 56, which is set to rinsing or cleaning duration of about 1 minute by a time control valve in the control unit A3, is opened; the RINSE indicator 115 (blue) is activated thereby. The setting of the rinsing or cleaning duration to about 1 minute corresponds to the general rule; however, the rinsing or cleaning period can be prolonged if necessary. In addition, the rinsing or cleaning operation or process can be repeated once or several times in the case of heavy contamination. If the rinsing or cleaning operation or process is intended to be repeated, the toggle switch 98 must be placed into the OFF position and thereafter back to the ON position, whereupon the rinsing or cleaning operation is restarted. This procedure is recommended, for example, when the electrode is intended to be stored in the clean condition at the end of the monitored fermentation process. The electrode remains immersed in water after the rinsing or cleaning operation. If the rinsing or cleaning water pressure is insufficient, the red alarm indicator 116 is activated and continues to be activated until the rinsing or cleaning water pressure is increased. Thereafter, the rinsing or cleaning operation must be repeated. The "CALIBRATION" program or calibrating operation is blocked during the time the rinsing or cleaning water pressure is insufficient.

After completion of the rinsing or cleaning operation and in the ON position of the aforementioned toggle switch 102, the first buffer solution having pH 7 is automatically pumped from the first storage vessel 60 into the rinsing chamber 5 by means of the first metering pump 68 via the feed conduit 38 and the check valve 44. Thereafter, the pneumatic request indicator 106 of the control unit A3 shows the request to set pH 7 using the amplifier 117. As soon as this pH is reached, the pneumatic indicator 111 shows the request to initiate the further course of the operation by means of the ACKNOWLEDGE control element 110. The pH electrode 6 is thereby caused to be rinsed for about 10 seconds whereafter the second buffer solution of, for example, pH 4.01 is pumped from the second storage vessel 62 into the rinsing chamber 5 by means of the second metering pump 74 via the feed conduit 40 and the check valve 46. Thereafter the pneumatic request indicator 108 of the control unit A3 shows the request to set the pH to the value of 4.01 using the control or regulator at the amplifier 117.

If the filling state of the first storage vessel 60 and/or the second storage vessel 62 is insufficient, the sensor 64 and/or the sensor 65 transmits a signal to the control unit A3 via the compressed air conduits 66 and 67, whereby the red alarm indicator 118 BUFFER SOLUTION is activated. This indication is extinguished only when the storage vessels 60 and/or 62 are filled. Only then the calibration program can be started.

After completion of the calibration program, such calibration program can be repeated, if desired, by operating the toggle switch 102, but this is only appropriate if the pH electrode 6 shows unclear results. Otherwise, the pH electrode 6 can be re-introduced into the fluid medium to be investigated by operating the push button 94. During this operation the shut-off device 10 is opened. After insertion of the pH electrode 6 into the fluid medium to be investigated, the instant measured pH value appears at the LCD display 114 and the indication MEASUREMENT (green) appears at the pneumatic indicator 112.

Simple and trouble-free execution of the entire maintenance operation is ensured by continuously monitoring the rinsing or cleaning water pressure, on the one hand, and the quantity of the buffer solutions present in the first and second storage vessels 60 and 62, the immediate indication of occurring malfunctions due to the lighting of alarm signals in the display part of the control unit A3, and the continuous indication of the current status of the program course. The temperature of the first and second buffer solutions, on the one hand, and the temperature of the fluid medium to be investigated can be respectively automatically compensated for by the temperature compensation resistance 24, which is arranged in the rinsing chamber 5 or electrode space, and the aforementioned further temperature compensation resistance in the fluid medium to be investigated. Both these temperature compensation resistances are coupled to the control unit A3. As a result, measurement errors which are caused by temperature differences, can be eliminated. Such temperature differences also can be manually compensated by operating the control element 128.

While there are shown and described present preferred embodiments of the invention, it is to be distinctly understood that the invention is not limited thereto, but may be otherwise variously embodied and practiced within the scope of the following claims.

I claim:

1. A maintenance device for at least partial automatic cleaning and calibration of a probe which is part of a measuring device for continuously monitoring biological or chemical processes by measuring analytical parameters in a fluid medium to be investigated, comprising:

a measured value transmitter unit including the probe;

said probe containing a measured value transmitter;

a sensor of said probe being operatively connected to said measured value transmitter;

an external tube of said probe;

a guide device of said probe being associated with said external tube and holding and guiding said sensor of said probe in said external tube;

pneumatically operated displacement means of said probe being responsive to pneumatic signals and acting upon said guide device such as to displace said sensor of said probe between an operative position, in which said sensor of said probe is immersed into the fluid medium to be investigated, and a maintenance position, in which said sensor of said probe is placed outside said fluid medium to be investigated;

a shut-off device for closing said probe to said fluid medium to be investigated;

a metering unit for feeding at least one rinsing fluid and at least one buffer as calibration fluid;

a control unit for having control elements for emission of pneumatic signals for controlling the operation of the measured value transmitter unit and the operation of the metering unit;

said control unit further containing indicators for indicating the operational states and malfunctions in the operation of the measured value transmitter unit and the metering unit; and the measured value transmitter unit and the metering unit being coupled to the control unit by means of compressed air conduits for tramsmitting the pneumatic signals.

2. The maintenance device as defined in claim 1, wherein;

said pneumatically operated displacement means contain an actuating member for displacing the sensor of said probe; and said actuating member being coupled to the shut-off device and said guide device and being controlled by said pneumatic signals emitted by the control unit.

3. The maintenance device as defined in claim 1 or claim 2, wherein:

said metering unit contains:

a feed system for feeding said at least one rinsing fluid and said at least one buffer solution as calibration fluid;

said feed system being equipped with a pressure controller coupled to the control unit via related ones of said compressed air conduits;

a directional control valve coupled to the control unit via a related one of said compressed air conduits;

a first storage vessel equipped with a sensor and containing a first buffer solution;

a second storage vessel equipped with a sensor and containing a second buffer solution;

a first metering pump for metering the first buffer solution;

a second metering pump for metering the second buffer solution;

the sensors being coupled to the control unit via related ones of said compressed air conduits;

the first metering pump being coupled to the control unit via related ones of said compressed air conduits; and the second metering pump coupled to the control unit via ones of said compressed air conduits.

4. The maintenance device as defined in claim 3, wherein:

the control unit comprises control elements for controlling:

(i) the displacement of the sensor of said probe between said operative position and said maintenance position, and (ii) selectively either one of an initiation or a repetition of feeding said at least one rinsing fluid and said at least one buffer solution from said metering unit to said measured value transistor unit in order to thereby respectively carry out cleaning and calibrating operations on said sensor of said probe.

5. The maintenance device as defined in claim 4, wherein:

said indicators of said control unit comprise pneumatic indicators for indicating the current position of the sensor of said probe and thereby the respective operational states of the measured value transmitter unit, pneumatic indicators for indicating the respective feeding operational states of the metering unit, and alarm indicators for indicating malfunctions in the metering unit during the respective feeding operations of the at least one rinsing fluid and the at least one buffer solution.

6. The maintenance device as defined in claim 5, further including:

a temperature compensation resistance arranged in the probe and provided for compensation of temperature variations in the buffer solutions;

another temperature compensation resistance arranged in the fluid medium to be investigated and provided for compensation of temperature variations in the measured medium; and said temperature compensation resistance being connected to said control unit.

7. The maintenance device as defined in claim 1 wherein:

the control unit is coupled to a central compressed air supply.

8. The maintenance device as defined in claim 1, wherein:

the compressed air conduits are equipped with solenoid valves to be operated electrically;

PE transducers for converting pneumatic signals into electrical signals; and the control unit is connected to a central process control.

9. The maintenance device as defined in claim 1, wherein:

the sensor of said probe is an electrochemical sensor.

10. The maintenance device as defined in claim 9, wherein:

said electrochemical constitutes a pH electrode.

11. The maintenance device as defined in claim 1, wherein:

the sensor of said probe is an optical sensor.

* * * * *

UNITED STATES PATENT AND TRADEMARK OFFICE
CERTIFICATE OF CORRECTION

PATENT NO. : 4,852,385
DATED : August 1, 1989
INVENTOR(S) : HEINZ JüRGEN BRINKMANN It is certified that error appears in the above-identified patent and that said Letters Patent is hereby corrected as shown below:

Column 3, line 14, after "measured" delete "valve" and insert --value--

Column 6, line 11, after "closed." please make a new paragraph

Column 7, line 55, after "unit" please delete "43" and insert --A3--

Column 9, please delete line 66 in its entirety

Column 9, line 66, please insert --What I claim is--

Column 10, line 26, after ""buffer"" please insert --solution--

Column 10, line 27, after "unit" please delete "for"

Column 11, line 4, after "pump" please insert --being--

Signed and Sealed this

Seventh Day of August, 1990

Attest:

HARRY F. MANBECK, JR.

*Attesting Officer*  *Commissioner of Patents and Trademarks*